(12) United States Patent
Hanson

(10) Patent No.: US 10,058,596 B2
(45) Date of Patent: Aug. 28, 2018

(54) COMPOSITION FOR ENZYMATIC DEBRIDEMENT

(71) Applicant: KCI Licensing, Inc., San Antonio, TX (US)

(72) Inventor: Douglas Philip Hanson, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 392 days.

(21) Appl. No.: 13/719,176

(22) Filed: Dec. 18, 2012

(65) Prior Publication Data

US 2013/0156745 A1 Jun. 20, 2013

Related U.S. Application Data

(60) Provisional application No. 61/577,997, filed on Dec. 20, 2011.

(51) Int. Cl.

| | | |
|---|---|---|
| *A61K 38/43* | (2006.01) | |
| *A61K 9/00* | (2006.01) | |
| *A61K 9/06* | (2006.01) | |
| *A61K 38/48* | (2006.01) | |

(52) U.S. Cl.
CPC ............ *A61K 38/43* (2013.01); *A61K 9/0014* (2013.01); *A61K 9/06* (2013.01); *A61K 38/4873* (2013.01)

(58) Field of Classification Search
None
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Erin M. Bowers

(57) ABSTRACT

Methods and compositions for the enzymatic debridement of wounds are provided. Methods for preparing enzymatic debridement compositions are also provided. In one embodiment, an enzymatic debridement composition prepared by dissolving crude bromelain in a composition comprising a weak acid, and filtering and/or dialyzing the dissolved crude bromelain to obtain the enzymatic debridement composition is provided.

14 Claims, 2 Drawing Sheets

(56) References Cited

U.S. PATENT DOCUMENTS

| | | |
|---|---|---|
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,197,291 A | 4/1980 | Klein et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,387,517 A | 2/1995 | Cini |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0102253 A1 | 8/2002 | Mynott et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0148429 A1* | 6/2009 | Gorecki ............ A61K 31/00 424/94.6 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/010424 | 9/1990 |
| WO | WO 93/009727 | 5/1993 |
| WO | WO 94/020041 | 9/1994 |
| WO | WO 96/05873 | 2/1996 |
| WO | WO 97/18007 | 5/1997 |
| WO | WO 99/13793 | 3/1999 |

OTHER PUBLICATIONS

Louis C. Argenta, Md and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, Md, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

(56) References Cited

OTHER PUBLICATIONS

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.
G. Živadinović, V. Ðukia, Ž. Maksimović, Ð. Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, "*Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion of the International Searching Authority dated Feb. 25, 2013, by the European Patent Office as the International Searching Authority in corresponding International Patent Application No. PCT/US2012/070412.

\* cited by examiner

COMPOSITION FOR ENZYMATIC DEBRIDEMENT

CROSS-REFERENCE TO RELATED APPLICATION

This application claims priority to U.S. Provisional Application No. 61/577,997, filed Dec. 20, 2011,entitled COMPOSITION FOR ENZYMATIC DEBRIDEMENT, the disclosure of which is hereby incorporated by reference in its entirety.

BACKGROUND

Field

This disclosure relates generally to the field of wound care. More particularly, it concerns methods and compositions for enzymatic debridement of wounds.

Description of Related Art

Debridement is an important part of the healing process for certain types of wounds. A variety of techniques have been employed in the removal of dead, damaged, or infected tissue from wounds including surgical, mechanical, chemical, and enzymatic techniques. Enzymatic debridement uses naturally occurring enzymes to digest the dead, damaged, or infected tissue. Several enzymatic debriding agents have been developed including collagenase (Santyl®), papain/urea (Accuzyme® (discontinued)), fibrinolysin/DNAse (Elase), and trypsin (Vasolex®).

Extracts derived from the pineapple plant (*Ananas comosus*) have also been investigated as debridement agents. See, e.g., U.S. Pat. Nos. 4,197,291; 4,226,854; 4,329,430; 4,307,081; 5,106,621; 5,387,517; 5,830,739;and U.S. Publ. No. 2009/0148429.These efforts, however, have largely focused on isolating specific proteases or molecular weight fractions, which requires extensive processing of bromelain. Accordingly, there is a need for effective enzymatic debridement agents that can be obtained in large quantities and with relatively few processing steps.

SUMMARY

Provided herein are methods of preparing an enzymatic debridement composition from crude bromelain and enzymatic debridement compositions prepared by the disclosed methods. The methods include dissolving crude bromelain in a composition comprising one or more weak acids and removing low molecular weight components from the dissolved bromelain composition to obtain an enzymatic debridement composition. In one embodiment, removing the low molecular weight components from the dissolved bromelain composition involves filtration and/or dialysis. In another embodiment, the weak acid is acetic acid.

In one embodiment, provided herein is a method of preparing an enzymatic debridement composition comprising: (a) dissolving crude bromelain in a composition comprising a weak acid; (b) filtering the dissolved crude bromelain to obtain a filtered bromelain composition; (c) dialyzing the filtered bromelain composition to obtain the enzymatic debridement composition; and (d) optionally lyophilizing the enzymatic debridement composition.

In another embodiment, provided herein is a method of preparing an enzymatic debridement composition consisting essentially of: (a) dissolving crude bromelain in a composition comprising a weak acid; (b) filtering the dissolved crude bromelain to obtain a filtered bromelain composition; (c) dialyzing the filtered bromelain composition to obtain the enzymatic debridement composition; and (d) optionally lyophilizing the enzymatic debridement composition.

In a further embodiment, provided herein is a method of preparing an enzymatic debridement composition comprising: (a) dissolving crude bromelain in a composition comprising a weak acid; (b) filtering and/or dialyzing the dissolved crude bromelain to obtain the enzymatic debridement composition; and (c) optionally lyophilizing the enzymatic debridement composition.

In another embodiment, provided herein is a method of preparing an enzymatic debridement composition consisting essentially of: (a) dissolving crude bromelain in a composition comprising a weak acid; (b) filtering and/or dialyzing the dissolved crude bromelain to obtain the enzymatic debridement composition; and (c) optionally lyophilizing the enzymatic debridement composition.

As used herein, "crude bromelain" refers to a precipitate obtained or obtainable by adding acetone at ~20% by volume to the juice from the stem of the pineapple plant.

As used herein, "a weak acid" refers to an acid that does not dissociate completely. It does not donate all of its protons (hydrogens) to the solution. Examples of weak acids include but are not limited to acetic acid, trichloroacetic acid, oxalic acid, formic acid, benzoic acid, and citric acid.

The amount of a weak acid used to dissolve the crude bromelain may be, for example, between about 0.1 to 1 M or between about 0.2 to 0.4 M. In certain embodiments, the acid composition comprises about 0.3 M weak acid.

Filtration is a process that removes contaminants and/or insoluble components from a fluid by passage through a porous substrate such as a membrane. In certain embodiments, the filter pore size may be about 0.1 to 10 µm, 0.1 to 1 µm, or 0.1 to 0.4 µm. In one embodiment, the dissolved crude bromelain is filtered through a 0.2 µm pore filter. In certain aspects, the filtration is assisted by applying a vacuum or pressure.

Dialysis separates molecules in solution by the difference in their rates of diffusion through a semipermeable membrane, such as dialysis tubing. In certain aspects, the filtered bromelain composition is subjected to dialysis to obtain the enzymatic debridement composition. In some embodiments, the filtered bromelain is dialyzed through a membrane having a molecular weight cut off of about, or at least, 7,000, 8,000, 10,000, 11,000, 12,000, 12,400, 13,000,or 14,000 Daltons. In some embodiments, the membrane has a molecular weight cut off of about 6,000-8,000 or 12,000-14,000 Daltons. In one embodiment, the filtered bromelain composition is subjected to dialysis using a 12,400 Dalton molecular weight cut-off membrane.

In some embodiments, the process steps for preparing the enzymatic debridement compositions are carried out at room temperature. In other embodiments, the steps for preparing the enzymatic debridement compositions are carried out below room temperature.

The enzymatic debridement composition may be formulated in a variety of ways such as, for example, a liquid, gel, powder, foam, paste, spray, or film. In certain aspects, the enzymatic debridement composition is lyophilized to a powder. The lyophilized enzymatic debridement composition may be used in powder form, or the powder may be further processed into gels, foams, aerosols, films, or other formulations. In certain embodiments, the amount of enzymatic debridement composition or lyophilized enzymatic debridement composition in a formulation may be between about 0.5 to 25%, 1 to 20%, 5 to 15%, or 8 to 12% by weight. In one embodiment, the amount of enzymatic debridement composition or lyophilized enzymatic debridement composition in a formulation is about 10% by weight. In some aspects, the enzymatic debridement composition is applied to a wound dressing, such as a gauze, cloth, or film.

The methods and compositions provided herein therefore also relate to a wound dressing comprising an enzymatic debridement composition or formulation thereof as disclosed herein and a formulation (such as a liquid, gel, powder, foam, paste, spray, or film) comprising an enzymatic debridement composition as disclosed herein, optionally in an amount of about 0.5 to 25%, 1 to 20%, 5 to 15%, or 8 to 12% by weight.

In a further embodiment, provided herein is a method of preparing an enzymatic debridement composition consisting essentially of: (a) dissolving crude bromelain in a composition comprising 0.3M of a weak acid; (b) filtering the dissolved crude bromelain through a 0.2 µm pore filter to obtain a filtered bromelain composition; (c) dialyzing the filtered bromelain composition through a 12,400 molecular weight cut-off membrane to obtain the enzymatic debridement composition; and (d) lyophilizing the enzymatic debridement composition. The composition may then be further formulated.

In another embodiment, provided herein is an enzymatic debridement composition prepared by a method comprising: (a) dissolving crude bromelain in a composition comprising a weak acid; (b) filtering and/or dialyzing the dissolved crude bromelain to obtain an enzymatic debridement composition; and (c) optionally lyophilizing the enzymatic debridement composition. In one embodiment, the method of preparing the enzymatic debridement composition comprises filtering the dissolved bromelain to obtain a filtered bromelain composition, and dialyzing the filtered bromelain composition to obtain the enzymatic debridement composition.

In some embodiments, the weak acid used in the preparation of the enzymatic debridement compositions is selected from the group consisting of acetic acid, trichloroacetic acid, oxalic acid, formic acid, benzoic acid, citric acid, and a mixture thereof. In other embodiments, the weak acid is acetic acid.

In a further embodiment, provided herein is a pharmaceutical composition comprising: (a) an enzymatic debridement composition, wherein the enzymatic debridement composition was prepared by dissolving crude bromelain in a composition comprising a weak acid, and filtering and/or dialyzing the dissolved crude bromelain to obtain the enzymatic debridement composition, and optionally lyophilizing the enzymatic debridement composition; and (b) an excipient. In some embodiments, preparing the enzymatic debridement composition comprises filtering the dissolved bromelain to obtain a filtered bromelain composition; and dialyzing the filtered bromelain composition to obtain the enzymatic debridement composition.

The pharmaceutical composition may be formulated as, for example, a liquid, gel, powder, foam, spray, or film. The excipient may be any pharmaceutically acceptable carrier that is compatible with the enzymatic debridement composition. Non-limiting examples include water, saline solutions such as normal saline, Ringer's solution, glycerol, ethanol, PBS (phosphate-buffered saline), and generally mixtures of various salts including potassium and phosphate salts with or without sugar additives such as glucose. Nontoxic auxiliary substances, such as wetting agents, buffers, or emulsifiers may also be added to the composition.

The amount of a weak acid used to dissolve the crude bromelain may be, for example, between about 0.1 to 1 M or between about 0.2 to 0.4 M. In certain embodiments, the acid composition comprises about 0.3 M of a weak acid. In certain embodiments, the filter pore size may be about 0.1 to 10 µm, 0.1 to 1 µm, or 0.1 to 0.4 µm. In one embodiment, the dissolved crude bromelain is filtered through a 0.2 µm pore filter. In certain aspects, the filtration is assisted by applying a vacuum or pressure. In certain aspects, the filtered bromelain composition is subjected to dialysis to obtain the enzymatic debridement composition. In some embodiments, the filtered bromelain is dialyzed through a membrane having a molecular weight cut off of about or at least 7,000, 8,000, 10,000, 11,000, 12,000, 12,400, 13,000, or 14,000 Daltons. In some embodiments, the membrane has a molecular weight cut off of about 6,000-8,000 or 12,000-14,000 Daltons. In one embodiment, the filtered bromelain composition is subjected to dialysis using a 12,400 Dalton molecular weight cut-off membrane.

The enzymatic debridement composition may be formulated in a variety of ways such as, for example, a liquid, gel, powder, foam, paste, spray, or film. In certain aspects, the enzymatic debridement composition is lyophilized to a powder. The lyophilized enzymatic debridement composition may be used in powder form, or the powder may be further processed into gels, foams, aerosols, films, or other formulations. In certain embodiments, the amount of enzymatic debridement composition or lyophilized enzymatic debridement composition in a formulation may be between about 0.5 to 25%, 1 to 20%, 5 to 15%, or 8 to 12% by weight. In one embodiment, the amount of enzymatic debridement composition or lyophilized enzymatic debridement composition in a formulation is about 10% by weight. In another embodiment, the composition is in the form of a gel comprising about 10% of the enzymatic debridement composition by weight. In some aspects, the enzymatic debridement composition is applied to a wound dressing, such as a gauze, cloth, or film.

In another embodiment, provided herein is an enzymatic debridement composition comprising all acid soluble components of crude bromelain having molecular weights greater than about 12,000, 12,400, 13,000,or 14,000 Daltons, and being substantially devoid of components of crude bromelain having molecular weights less than about 12,000, 12,400, 13,000,or 14,000 Daltons. In some embodiments, the enzymatic debridement composition is lyophilized.

In one embodiment, provided herein is a method for debridement of devitalized tissue from a subject comprising: (a) contacting devitalized tissue with an enzymatic debridement composition to dissolve the devitalized tissue, wherein the enzymatic debridement composition was prepared by dissolving crude bromelain in a composition comprising a weak acid, and filtering and/or dialyzing the dissolved crude bromelain to obtain the enzymatic debridement composition, and optionally lyophilizing the enzymatic debridement composition; and (b) removing the dissolved devitalized tissue. In one embodiment, the method of preparing the enzymatic debridement composition comprises filtering the dissolved bromelain to obtain a filtered bromelain composition, and dialyzing the filtered bromelain composition to obtain the enzymatic debridement composition.

The methods and compositions provided herein further relates to an enzymatic debridement composition, as disclosed herein, for use in debridement of devitalized tissue from a subject.

The enzymatic debridement composition may be applied to the devitalized tissue as needed to dissolve the tissue. For example, in some embodiments the enzymatic debridement composition may be in contact with the devitalized tissue for about 1 to 48 hours, 1 to 24 hours, 1 to 12 hours, 1 to 8 hours, 1 to 4 hours, 2 to 48 hours, 2 to 24 hours, 2 to 12 hours, 2 to 8 hours, or 2 to 4 hours before the dissolved devitalized tissue is removed. In certain embodiments, the enzymatic debridement composition is in contact with the devitalized tissue for at least 1, 2, 3, 4, 5, 6, 7, 8, 12,or 24 hours before the dissolved devitalized tissue is removed. The steps of contacting the devitalized tissue with an enzymatic debridement composition to dissolve the devitalized tissue, and removing the dissolved devitalized tissue may be repeated as needed to effect the removal of the devitalized tissue. For example, the process may be repeated at least 1, 2, 3, 4, 5, 6, 7, 8, 9,or 10 times.

The method for applying the enzymatic debridement composition to the devitalized tissue may vary depending on factors such as the location and amount of devitalized tissue and the size and shape of the wound where the devitalized tissue is located. For example, a gel formulation may be desirable where large surface areas need to be covered, a coated foam formulation may be desirable for applications used with negative pressure therapy, and a coated gauze formulation may be desirable for areas that need to be wrapped. A health care provider will be able to determine an appropriate method for applying the enzymatic debridement composition to the devitalized tissue in view of such factors. In certain embodiments, the enzymatic debridement composition is applied by coating the devitalized tissue with the enzymatic debridement composition, or by injecting the enzymatic debridement composition into the devitalized tissue. The devitalized tissue may be covered with a wound dressing after the enzymatic debridement composition. In certain aspects, the wound dressing comprises the enzymatic debridement composition (e.g., gauze soaked in or coated with the enzymatic debridement composition), in which case the enzymatic debridement composition may be applied to the devitalized tissue by applying the wound dressing to the devitalized tissue. The dissolved devitalized tissue may be removed if by, for example, wiping or rinsing the dissolved tissue from the wound.

The wound may be any type of wound including, without limitation, a burn wound, sunburn, frostbite, diabetic ulcer, pressure ulcer, surgery site, or skin graft site.

Provided herein is a kit comprising the enzymatic debridement compositions or formulations disclosed herein. In certain embodiments, the kit may further comprise a wound dressing, such as a gauze, gel, foam, cloth, or film.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this specification, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the methods and compositions provided herein will become apparent from the following detailed description. It should be understood, however, that the detailed description and the specific examples, while indicating specific embodiments, are given by way of illustration only, since various changes and modifications within the spirit and scope will become apparent to those skilled in the art from this detailed description.

BRIEF DESCRIPTION OF THE DRAWINGS

The following drawings form part of the present specification and are included to further demonstrate certain embodiments. The methods and compositions disclosed herein may be better understood by reference to one or more of these drawings in combination with the detailed description of specific embodiments presented herein.

DESCRIPTION OF ILLUSTRATIVE EMBODIMENTS

A. Enzymatic Debridement Agents

Certain embodiments provide enzymatic debridement compositions and methods of preparing such compositions from bromelain. The compositions provided herein are the enzymatic debridement agents used for debridement purposes. Debridement is an important part of the healing process for certain types of wounds, and a variety of techniques have been employed in the debridement of wounds. Enzymatic debridement uses naturally occurring enzymes to digest the dead, damaged, or infected tissue. Several enzymatic debriding agents have been developed including collagenase (Santyl®), papain/urea (Accuzyme® (discontinued)), fibrinolysin/DNAse (Elase), and trypsin (Vasolex®).

Extracts derived from the pineapple plant (*Ananas comosus*) have also been investigated as debridement agents. See, e.g., U.S. Pat. Nos. 4,197,291; 4,226,854; 4,329,430; 4,307,081; 5,106,621; 5,387,517; 5,830,739; and U.S. Publ. No. 2009/0148429.These efforts, however, have largely focused on isolating specific proteases or molecular weight fractions, which requires extensive processing of bromelain. In addition to containing proteases, crude bromelain also contains protease inhibitors. For example, Perlstein and Kezdy (1973) identified seven closely related protease inhibitors, i.e., bromelain inhibitors I-VII, from a commercial bromelain acetone powder. These inhibitors were reported to have molecular weights of 5000-6000 Daltons.

The bromelain-based enzymatic debridement compositions provided herein remove devitalized tissue faster than Santyl®, Accuzyme®, and crude bromelain, yet can be prepared with fewer processing steps than needed to isolate specific proteases from crude bromelain. In general, the process of preparing the enzymatic debridement composition comprises: (a) dissolving crude bromelain in an acidic composition; and (b) filtering and/or dialyzing to obtain the enzymatic debridement composition. In some embodiments, the process of preparing the enzymatic debridement composition comprises filtering the dissolved bromelain to obtain a filtered bromelain composition, and dialyzing the filtered bromelain composition to obtain the enzymatic debridement composition. The enzymatic debridement composition may further be lyophilized to a powder.

In one embodiment, the acidic composition used to dissolve the crude bromelain comprises one or more weak acids. Examples of weak acids include but are not limited to acetic acid, trichloroacetic acid, oxalic acid, formic acid, benzoic acid, and citric acid. In another embodiment, the acidic composition comprises acetic acid.

Figure 1:
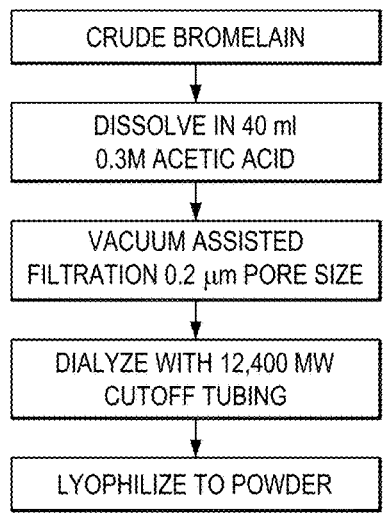
FIG. 1 shows a process for obtaining a lyophilized enzymatic debridement composition.

FIG. 1 shows a flow chart of one process of preparing the enzymatic debridement composition. As can be seen in FIG. 1, crude bromelain is first dissolved in 0.3M acetic acid. The dissolved bromelain is then filtered through a 0.2 μm pore size filter with vacuum assistance. After filtering, the composition is dialyzed with 12,400 MW cutoff tubing, and then lyophilized to a powder.

Filtration of the dissolved crude bromelain is used to remove the non-soluble components in the acidic solution. For example, a 2 micron filter will remove bacteria from the solution as well as most fat globules and insoluble protein aggregates, whereas most soluble proteins should pass through the filter.

Examples of some filtration techniques that are employed in the methods disclosed herein include gravimetric and pressure assisted techniques, such as but not limited to ultrafiltration.

Dialysis uses a semi-permeable membrane for diffusion of molecules from high concentration to low concentration. Only those molecules small enough to fit through the pores of the membrane will diffuse across the membrane. In the preparation of the enzymatic debridement compositions described here, small molecules (e.g., molecules with molecular weights less than about 12,400 Daltons) diffuse across the dialysis membrane and the larger-sized molecules are retained. By removing the low molecular weight components from the composition, the low molecular weight protease inhibitors can be substantially eliminated while retaining a broad range of active enzymes in the composition.

Examples of some dialysis techniques that may be employed in the methods disclosed herein include batch and continuous dialysis.

The enzymatic debridement composition is highly specific to necrotic tissue and will not digest the surrounding living tissue. The enzymatic debridement composition is also very fast and effective, removing nearly all necrotic tissue in as little as 4 hours. The speed at which this composition works is not merely an issue of convenience, but it also lessens the possibility of infection at the wound site and subsequent sepsis that can put a patient's life at risk.

B. Formulations

Provided herein are pharmaceutical compositions comprising the enzymatic debridement compositions (or agents) prepared by the methods disclosed herein. The enzymatic debridement compositions are provided in a variety of forms, particularly forms suitable for topical delivery to wound sites. For example, the enzymatic debridement compositions are formulated as liquids, gels, powders, pastes, foams, sprays, or films. In certain embodiments, the enzymatic debridement composition is first prepared as a powder, which is then further formulated into, for example, a gel, paste, foam, spray, or film.

The excipient(s) in the formulation may be any pharmaceutically acceptable carrier that is compatible with the enzymatic debridement composition. Non-limiting examples include water, saline solutions such as normal saline, Ringer's solution, glycerol, ethanol, PBS (phosphate-buffered saline), and generally mixtures of various salts including potassium and phosphate salts with or without sugar additives such as glucose. Nontoxic auxiliary substances, such as wetting agents, buffers, or emulsifiers may also be added to the composition. The formulation may be aqueous or non-aqueous. In one embodiment, the enzymatic debridement composition is in an aprotic deliver system.

In certain aspects, the enzymatic debridement composition is lyophilized to a powder. The lyophilized enzymatic debridement composition may be used in powder form, or the powder may be further processed into gels, foams, aerosols, films, or other formulations. In certain embodiments, the amount of enzymatic debridement composition or lyophilized enzymatic debridement composition in a formulation may be between about 0.5 to 25%, 1 to 20%, 5 to 15%, or 8 to 12% by weight. In one embodiment, the amount of enzymatic debridement composition or lyophilized enzymatic debridement composition in a formulation is about 10% by weight. In other embodiments, the enzymatic debridement composition or the lyophilized enzymatic debridement composition is in the form of a gel, and the gel comprises 10% by weight of the enzymatic debridement composition. In some aspects, the enzymatic debridement composition is applied to a wound dressing, such as a gauze, cloth, or film.

The enzymatic debridement composition may also be applied to or incorporated into a wound dressing, such as a gauze, cloth, or film. For example, the wound dressing could be saturated with the enzymatic debridement composition or the enzymatic debridement composition could be applied to one side of the wound dressing.

C. Wound Treatment

Wound healing depends on orderly progression through four known phases. These phases are hemostasis, inflammation, proliferation, and remodeling or maturation. In certain cases, a wound fails to heal in the orderly, predictable stages within the time expected. Such wounds are considered chronic, and sufferers of chronic wounds may have additional emotional and physical stress due to the failure of the wound to heal. Typically, a chronic wound develops if something causes disruption of the inflammatory phase or the proliferative phase. Common sources of disruption include infection, tissue hypoxia, repeated trauma, the presence of debris and/or necrotic tissue, and certain diseases such as diabetes. Patients with chronic wounds are at higher risk for infection, and often report a great deal of pain.

Debridement of dead or infected tissue (i.e., devitalized tissue) from the wound improves the healing potential of the remaining healthy tissue. The enzymatic debridement compositions disclosed herein are very fast and effective, capable of removing nearly all necrotic tissue from a wound within hours. Additionally, the compositions are highly specific to necrotic tissue and will not digest the surrounding healthy tissue. The method for applying the enzymatic debridement composition to the devitalized tissue may vary depending on factors such as the location and amount of devitalized tissue and the size and shape of the wound where the devitalized tissue is located. A health care provider will be able to determine an appropriate method for applying the enzymatic debridement composition to the devitalized tissue in view of such factors.

For example, the enzymatic debridement composition may be applied by coating the devitalized tissue with the enzymatic debridement composition. The enzymatic debridement composition may also be injected into the devitalized tissue. The wound may be covered with a wound dressing after the enzymatic debridement composition is applied. In certain aspects, the wound dressing comprises the enzymatic debridement composition (e.g., gauze soaked in or coated with the enzymatic debridement composition), in which case the enzymatic debridement composition may be applied to the devitalized tissue by applying the wound dressing to the devitalized tissue.

After the enzymatic debridement composition has been in contact with the wound for a desired amount of time, the dissolved devitalized tissue is removed, typically by wiping or rinsing the dissolved tissue from the wound. The enzymatic debridement composition may be re-applied as needed to remove any remaining devitalized tissue from the wound.

D. Kits

Provided herein are kits containing components for use in wound debridement. Any of the components disclosed herein may be combined in a kit. In certain embodiments, the kit comprises an enzymatic debridement compositions or formulations disclosed herein. The kit may further comprise a wound dressing, such as a gauze, cloth, or film.

The kits will generally include at least one vial, test tube, flask, bottle, syringe, foil package, or other container, into which a component may be placed, and preferably, suitably aliquoted. Where there is more than one component in the kit, the kit also will generally contain a second, third or other additional containers into which the additional components may be separately placed. However, various combinations of components may be comprised in a container. The kits also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

E. Examples

The following examples are included to demonstrate preferred embodiments. It should be appreciated by those of skill in the art that the techniques, disclosed in the examples which follow, represent techniques discovered by the inventor to function well in the practice of the methods and compositions disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

1. Debridement Compositions

A powdered bromelain enzymatic debridement composition was prepared by the processes shown in FIG. 1. The powdered bromelain enzymatic debridement composition was then formulated into a gel at 10% weight loading. The gel was an aqueous gel of 2% COSMEDIA® (polyacrylate). This gel formulation is referred to as KCI F2 in the pig skin model studies below.

Crude bromelain was also lyophilized to powder form and formulated into a gel (2% COSMEDIA® (polyacrylate)) at 10% weight loading. This gel formulation is referred to as KCI F1 in the pig skin model studies below.

2. Pig Skin Burn Model

The debridement compositions were evaluated using a pig skin burn model in which a blow torch is applied to fresh pig skin for 20 seconds to produce a patch of black eschar. The various debridement compositions were then applied to the eschar and covered with damp gauze. The skin was then placed in a sealed container in an oven at the 33° C. to simulate skin temperature. The skin remained in the oven for the duration of the testing periods indicated below.

After the testing period, the skin was removed from the oven and the dissolved tissue was gently wiped away. The results compare the histograms of images captured before and after treatment. The eschar was defined by the dark pixels, which were determined by masking to be in the range of 0-70.

3. Results

Figure 2:
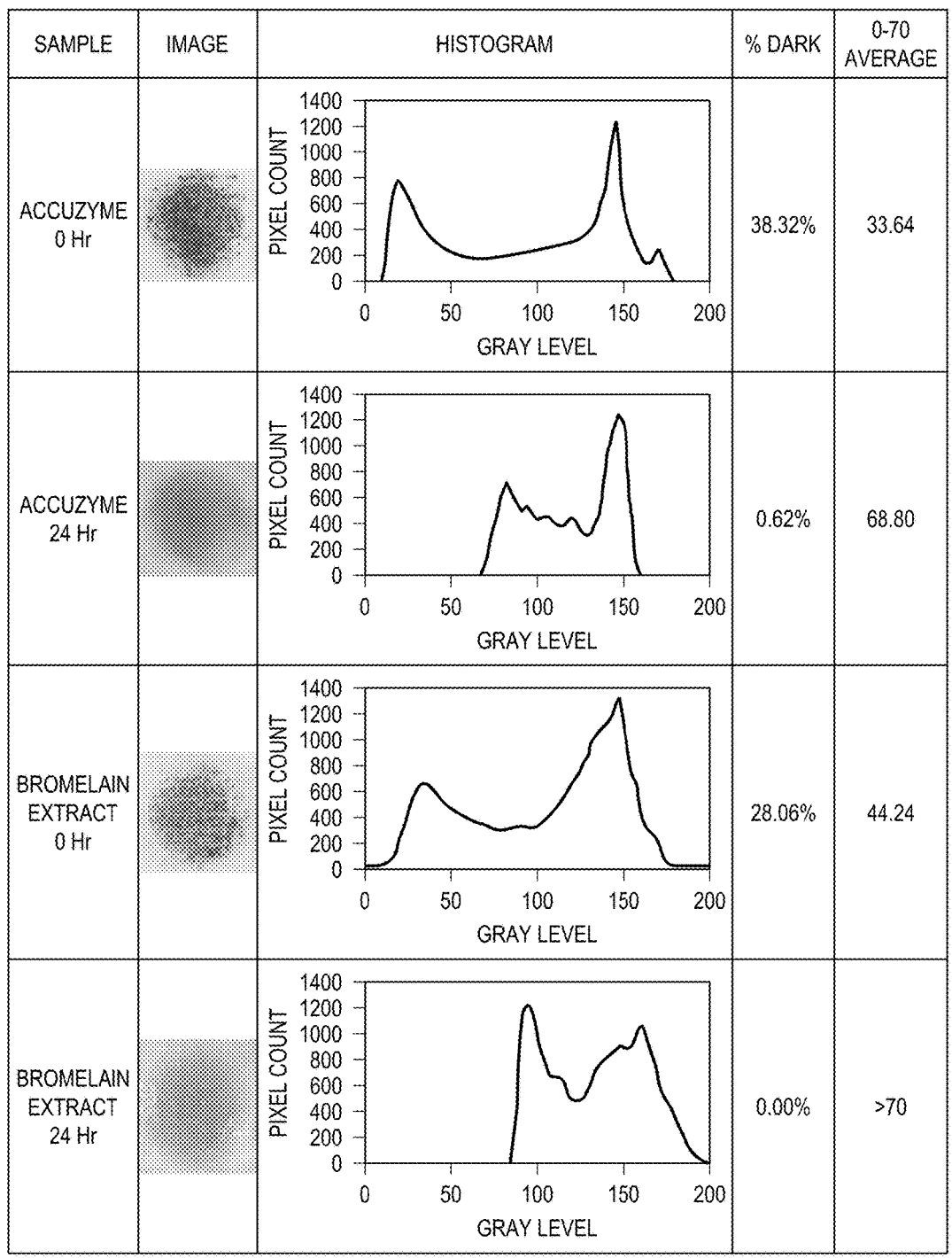
FIG. 2 shows a comparison of Accuzyme® (papain/urea) and a bromelain enzymatic debridement composition on a pig skin burn model over a 24 hour period.

The ability of KCI F2 and Accuzyme® (papain/urea) to remove the eschar in the burned pig skin model in 24 hours was evaluated. As shown in FIG. 2, the % Dark pixels at time 0 was 38.32% and 28.06% for the eschars treated with Accuzyme® (papain/urea) and KCI F2,respectively. Both Accuzyme® (papain/urea) and KCI F2 had completely dissolved the necrotic burn eschar from the pig skin model 24 hours after treatment (FIG. 2).

Santyl® (collagenase) only removed 28.50% of the eschar in a 24 hour period. This represents a debridement rate of 1.19% per hour. KCI F2 was over 20 times faster than Santyl® (collagenase).

In a further study, the ability of KCI F2, KCI F1,and Accuzyme® (papain/urea) to remove the eschar in the burned pig skin model after 2, 4, 6,and 8 hours was evaluated. The results are shown in Table 1 below.

TABLE 1

The eschar was defined by the dark pixels, with the dark pixels at the 0 hour time point normalized to 100%.

|  | 0 hr | 2 hr | 4 hr | 6 hr | 8 hr |
| --- | --- | --- | --- | --- | --- |
| Accuzyme ® | 100% | 65.78% | 56.88% | 46.78% | 16.11% |
| KCI F1 | 100% | 79.96% | 47.92% | 10.04% | 2.59% |
| KCI F2 | 100% | 54.52% | 3.37% | 0.00% | 0.00% |

As shown in Table 1, KCI F2 had almost completely removed the necrotic burn eschar within 4 hours (3.37% eschar remaining), whereas 56.88% and 47.92% of the eschar remained after 4 hours on the Accuzyme® (papain/urea) and KCI F1 treated skin.

Figure 3:
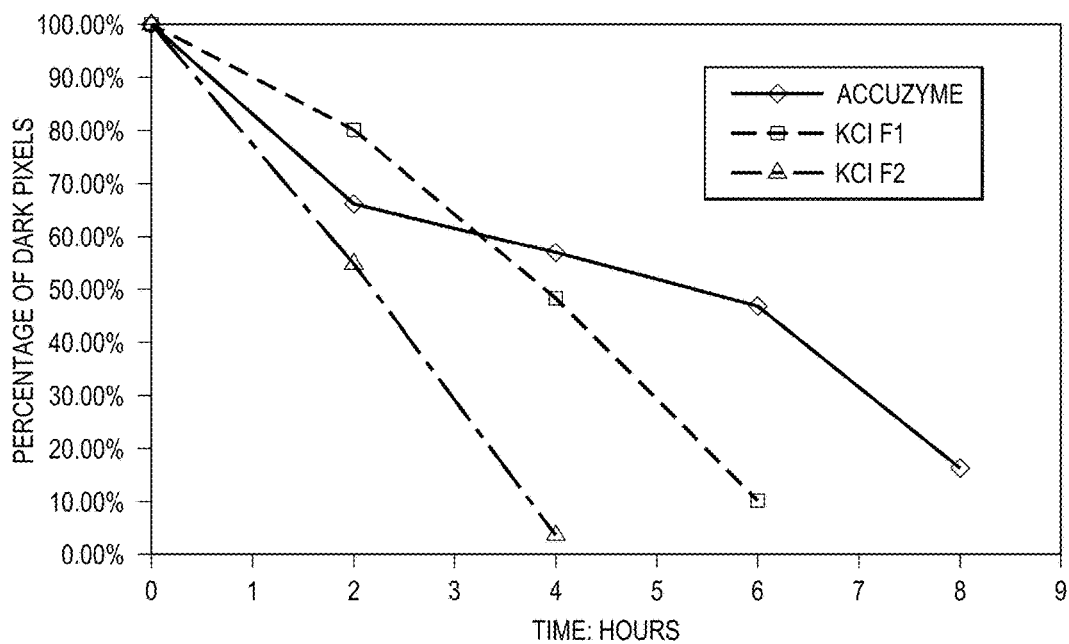
FIG. 3 shows a graph comparing Accuzyme® (papain/urea) and two bromelain formulations on a pig skin burn model from 0 to 8 hours at 2 hour intervals.

The amount of eschar remaining was plotted as a function of time in the graph shown in FIG. 3. This allowed the calculation of the removal rate by fitting the data to a straight line. KCI F2 had the fastest debridement rate at 24.20% per hour. The debridement rate for KCI F1 was 13.2% per hour. The debridement rate for Accuzyme® (papain/urea) was 9.3% per hour. Thus, the debridement rate for KCI F2 was 2.6 times faster than that of Accuzyme® (papain/urea).

\* \* \*

All of the compositions and methods disclosed and claimed herein can be made and executed without undue experimentation in light of the present disclosure. While the compositions and methods disclosed herein have been described in terms of certain embodiments, it will be apparent to those of skill in the art that variations may be applied to the compositions and methods and in the steps or in the sequence of steps of the methods described herein without departing from the concept, spirit and scope of the present disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

U.S. Pat. No. 4,197,291
U.S. Pat. No. 4,226,854
U.S. Pat. No. 4,307,081
U.S. Pat. No. 4,329,430
U.S. Pat. No. 5,106,621
U.S. Pat. No. 5,387,517
U.S. Pat. No. 5,830,739
U.S. Publ. No. 2009/0148429
Perlstein and Kezdy, J. Supramol. Struct., 1: 249-254, 1973.

The invention claimed is:

1. A method of preparing an enzymatic debridement composition wherein the method consists of:
   (a) dissolving crude bromelain in a composition comprising a weak acid;
   (b) filtering and/or dialyzing the dissolved crude bromelain to obtain the enzymatic debridement composition; and
   (c) optionally lyophilizing the enzymatic debridement composition.

2. The method of claim 1, wherein the method consists of:
   (a) dissolving crude bromelain in a composition comprising a weak acid;
   (b) filtering the dissolved crude bromelain to obtain a filtered bromelain composition;
   (c) dialyzing the filtered bromelain composition to obtain the enzymatic debridement composition; and
   (d) optionally lyophilizing the enzymatic debridement composition.

3. The method of claim 1, wherein the weak acid is selected from the group consisting of acetic acid, trichloroacetic acid, oxalic acid, formic acid, benzoic acid, and citric acid.

4. The method of claim 1, wherein the enzymatic debridement composition is in the form of liquid or powder.

5. A method of preparing an enzymatic debridement composition wherein the method consists of:
   (a) dissolving crude bromelain in a composition comprising a weak acid;
   (b) filtering and/or dialyzing the dissolved crude bromelain to obtain the enzymatic debridement composition;
   (c) optionally lyophilizing the enzymatic debridement composition to obtain a lyophilized enzymatic debridement composition; and
   (d) formulating the lyophilized enzymatic debridement composition into a liquid, a powder, a film, a gel, a foam, or a spray.

6. The method of claim 5, wherein the gel comprises 10% by weight of the lyophilized enzymatic debridement composition.

7. The method of claim 3, wherein the crude bromelain is dissolved in a composition comprising 0.3M acetic acid.

8. The method of claim 1, wherein the dissolved crude bromelain is filtered through a 0.2μm pore filter.

9. The method of claim 1, wherein the filtered bromelain is dialyzed through a 12,400 molecular weight cut-off membrane.

10. A method of preparing an enzymatic debridement composition wherein the method consists of:
    (a) dissolving crude bromelain in a composition comprising a weak acid;
    (b) filtering and/or dialyzing the dissolved crude bromelain to obtain the enzymatic debridement composition;
    (c) optionally lyophilizing the enzymatic debridement composition to obtain a lyophilized enzymatic debridement composition; and
    (d) applying the enzymatic debridement composition or the lyophilized enzymatic debridement composition on a wound dressing.

11. A method for debridement of devitalized tissue from a subject consisting of:
    (a) dissolving crude bromelain in a composition comprising a weak acid;
    (b) filtering and/or dialyzing the dissolved crude bromelain to obtain the enzymatic debridement composition;
    (c) optionally lyophilizing the enzymatic debridement composition to obtain a lyophilized enzymatic debridement composition;
    (d) contacting the devitalized tissue with the enzymatic debridement composition or the lyophilized enzymatic debridement composition to dissolve the devitalized tissue; and
    (e) removing the dissolved devitalized tissue.

12. The method of claim 11, wherein the method consists of:
    (a) dissolving crude bromelain in a composition comprising a weak acid;
    (b) filtering the dissolved crude bromelain to obtain a filtered bromelain composition;
    (c) dialyzing the filtered bromelain composition to obtain the enzymatic debridement composition;
    (d) optionally lyophilizing the enzymatic debridement composition to obtain a lyophilized enzymatic debridement composition;
    (e) contacting the devitalized tissue with the enzymatic debridement composition or the lyophilized enzymatic debridement composition to dissolve the devitalized tissue; and
    (f) removing the dissolved devitalized tissue.

13. The method of claim 11, wherein the enzymatic debridement composition is in contact with the devitalized tissue for 1 to 48 hours before the dissolved devitalized tissue is removed.

14. The method of claim 11, wherein contacting the devitalized tissue is by coating the devitalized tissue with the enzymatic debridement composition or by injecting the enzymatic debridement composition into the devitalized tissue.

* * * * *